United States Patent
Semaan

(10) Patent No.: US 9,546,497 B2
(45) Date of Patent: Jan. 17, 2017

(54) LINK-PLATE CONNECTION FOR MONOPOLE REINFORCING BARS

(71) Applicant: Robert Semaan, Miami, FL (US)

(72) Inventor: Robert Semaan, Miami, FL (US)

( * ) Notice: Subject to any disclaimer, the term of this patent is extended or adjusted under 35 U.S.C. 154(b) by 0 days.

(21) Appl. No.: 14/552,263

(22) Filed: Nov. 24, 2014

(65) Prior Publication Data

US 2015/0075101 A1 Mar. 19, 2015

Related U.S. Application Data

(60) Provisional application No. 62/026,522, filed on Jul. 18, 2014.

(51) Int. Cl.
| | |
|---|---|
| *E04C 3/00* | (2006.01) |
| *E04H 12/22* | (2006.01) |
| *C01B 6/24* | (2006.01) |
| *C07B 31/00* | (2006.01) |
| *C07D 295/03* | (2006.01) |
| *E04C 5/06* | (2006.01) |

(52) U.S. Cl.
CPC .......... *E04H 12/2292* (2013.01); *C01B 6/24* (2013.01); *C07B 31/00* (2013.01); *C07D 295/03* (2013.01); *E04C 5/06* (2013.01)

(58) Field of Classification Search
CPC .......... E04H 12/2292; E04H 12/24; E04C 2003/026; Y10T 403/66; Y10T 403/50
USPC ............................................. 403/DIG. 15
See application file for complete search history.

(56) References Cited

U.S. PATENT DOCUMENTS

| | | | | |
|---|---|---|---|---|
| 278,617 | A * | 5/1883 | Smith ............... | F16L 37/0987 285/319 |
| 731,752 | A * | 6/1903 | Cadwell ............ | E04H 12/2292 52/295 |
| 2,963,127 | A * | 12/1960 | Manville ............ | E04B 2/56 248/188.91 |
| 3,077,009 | A * | 2/1963 | Hutchinson ......... | E04C 3/02 52/632 |
| 4,032,244 | A * | 6/1977 | Quayle ............... | E02D 5/523 403/286 |
| 4,645,228 | A * | 2/1987 | Bertonneau ......... | A63C 5/02 280/603 |
| 4,854,665 | A * | 8/1989 | Gagnon ............... | G02B 6/4459 285/903 |
| 4,987,718 | A * | 1/1991 | Knight ................ | E04H 12/2292 52/170 |
| 5,240,032 | A * | 8/1993 | Mizioch .............. | E03B 9/10 137/368 |
| 6,170,218 | B1 * | 1/2001 | Shahnazarian ...... | E04B 5/12 52/693 |
| 7,267,375 | B1 * | 9/2007 | Sorkin ................ | E04C 5/10 285/245 |
| 7,273,238 | B1 * | 9/2007 | Sorkin ................ | F16L 21/022 277/616 |
| 7,849,659 | B2 * | 12/2010 | Kopshever, Sr. .... | H01Q 1/1242 52/18 |
| 8,657,344 | B2 * | 2/2014 | Glazik ............... | E03F 5/0404 285/302 |

(Continued)

*Primary Examiner* — Brian Mattei
*Assistant Examiner* — Gisele Ford

(57) ABSTRACT

Reinforcing bars include load transfer connectors. A link plate includes openings that mate with the load transfer connectors to overlie the splice between reinforcing bars being spliced. A cover plate may be fastened over the link plate.

22 Claims, 3 Drawing Sheets

(56) References Cited

U.S. PATENT DOCUMENTS

| | | | | |
|---|---|---|---|---|
| 2004/0071507 | A1* | 4/2004 | Kim | E04C 5/165 403/368 |
| 2006/0228170 | A1* | 10/2006 | Joo | E04C 5/165 403/286 |
| 2012/0230757 | A1* | 9/2012 | Amikura | F16B 39/101 403/286 |
| 2012/0263554 | A1* | 10/2012 | Sanz Gamboa | B66B 7/026 411/81 |
| 2014/0083046 | A1* | 3/2014 | Yang | E04B 1/24 52/704 |

* cited by examiner

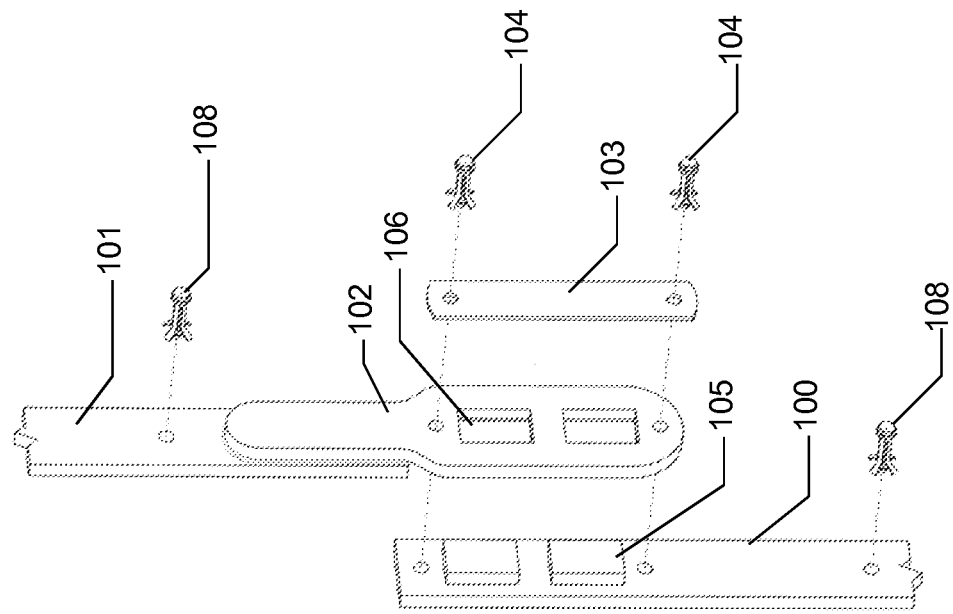
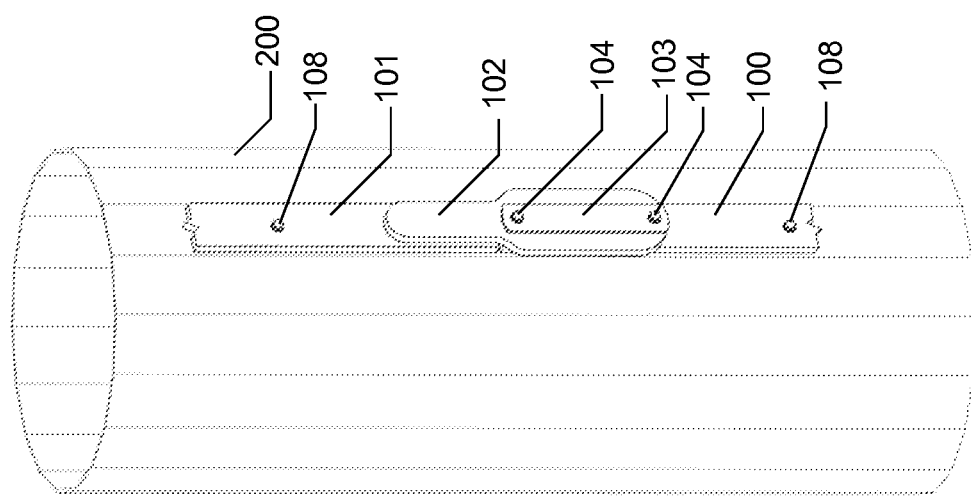

LINK-PLATE CONNECTION FOR MONOPOLE REINFORCING BARS

RELATED APPLICATION DATA

The present application claims the priority of U.S. Provisional Application Ser. No. 60/026,522, entitled "Link-plate Boltless Connection for Monopole Flat Plate Reinforcement," filed on Jul. 18, 2014 by Applicant herein.

FIELD OF THE INVENTION

The present application relates to methods and devices for reinforcing monopoles. More specifically, the present invention includes link-plates reinforcing plates/bars attached to monopoles, where the link-plates include holes that mate with blocks welded or loose to pole reinforcing plates to provide a positive connection for transferring the axial loads between the two reinforcing plates/bars.

BACKGROUND OF THE INVENTION

The wireless telecommunications industry has been growing steadily for a number of years. Consumers continue to demand more coverage, faster access and improved functionality of wireless devices. The advent of data (in addition to voice) has taxed the ability of current networks to support the increased traffic and wireless Carriers are deploying newer, larger and more complex antennas and equipment to increase capacity. This affects both new and existing sites.

New sites are designed to support the larger and heavier equipment—but building new sites is very expensive and is usually done as a last resort and only when coverage areas are to be extended. The more common practice is to use existing sites and to simply replace equipment and antennas as needed. However, existing sites were not always designed for the lateral loads caused by the wind forces on the additional equipment and the supporting monopole must be augmented structurally to allow for these larger antennas and equipment.

A common type of tower built in densely populated urban areas is the monopole. These monopoles are usually multi-sided or round tapered or straight tubular structures with a very small profile and hence more attractive from a zoning and siting approval standpoint. However, these are also the more difficult to augment or modify structurally since the bolting of additional structural elements must be done from the outside as they are too narrow to access from the inside.

One of the more common methods of strengthening these monopoles has been the addition of flat plates or bars to the "flats or flat sides" of the multi-sided structures. Similar concepts are used for cylindrical structures. While this is fairly simple using bolts that can be installed from the outside, the magnitude of the forces seen in the flat plates or bars require very large quantities of bolts at the splice connections between the flat plates or bars for load transfer. For example, a typical splice requires the use of eighteen or more splice bolts per splice per reinforcing plate. Thus, a four-sided plate augmentation design would require seventy-two bolts at each splice elevation. Reinforcing a monopole from the ground to a one-hundred twenty foot elevation may require five or more splices, resulting in more than four-hundred bolts and four-hundred bolt holes to be drilled in the air in the field. As may be appreciated, drilling bolt holes into the monopole and installing such flat plates at elevated heights can be very costly and labor intensive.

As wireless networks continue to tax the structural capacity of existing monopole structures structural augmentation of these structures with flat plate reinforcing solutions will continue.

SUMMARY OF THE INVENTION

Embodiments of the present invention include a device for reinforcing a monopole. In one optional embodiment, a device includes a plurality of reinforcing plates or bars each having ends and a surface. Each of the reinforcing plates or bars includes at least one or two load transfer connectors attached to the reinforcing bar, proximate to at least one of the ends. The load transfer connectors may be attached to the reinforcing bars (such as by welding) or may be integrally formed with the reinforcing bars or keyed in holes in the reinforcing bars. In one optional embodiment, the load transfer connectors are attached to the reinforcing bar surface. In another optional embodiment, the load transfer connectors may fit into openings in the reinforcing bar.

A device also includes a link-plate having one or more openings shaped to mate with the load transfer connectors. In this manner, adjoining reinforcing bars may be spliced by overlaying the link plate over the reinforcing bars and mating the link plate openings with the load transfer connectors (also referred to as shear blocks) of each adjoining reinforcing bar. In an optional embodiment, the mating connection between the link plate openings and the load transfer connectors may be an interference fit, as known as a press fit or a friction fit, as those terms are commonly understood in mechanical engineering.

In an optional embodiment, the device may further include cover plate positioned to overlie the link plate openings while mated with the load transfer connectors.

BRIEF DESCRIPTION OF THE DRAWINGS

FIG. 4 is an elevated perspective view of a pole and assembled link-plate according to an embodiment of the present invention;

FIG. 5 is an elevated perspective assembly view of a link-plate according to an embodiment of the present invention;

DESCRIPTION

Figure 3:
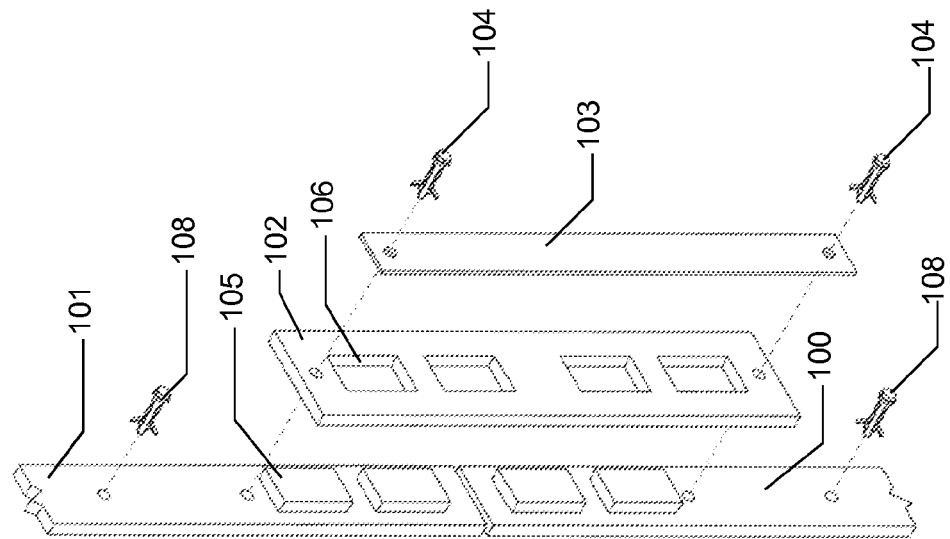
FIG. 3 is an elevated perspective assembly view of a link-plate according to an embodiment of the present invention.

Reference is now made to the figures wherein like parts are referred to by like numerals throughout. The present invention is a system for reinforcing a monopole which includes multiple reinforcing bars 100, 101. In the optional embodiment illustrated in FIGS. 1-8, each reinforcing bar 100, 101 includes an elongated, flat plate section, although the shape and dimensions of the reinforcing bars 100, 101 may vary depending on the optional embodiment. As illustrated in the figures, the plate sections of the reinforcing bars 100, 101 are sized and shaped to lie along the surface of a monopole 200. For example, in an optional embodiment in which the monopole 200 has a polygonal cross-section, the plate section of the reinforcing bars 100, 101 may be flat. In other optional embodiments in which the monopole 200 has a different shape, such as a cylindrical cross-section, the plate section of the reinforcing bars may have a different shape.

The reinforcing bars 100, 101 are secured to the monopole 200, optionally using bolts or other fasteners 108. As explained in greater detail below, the reinforcing bars 100, 101 are linked together to reinforce the monopole, whether the reinforcing bars are subjected to compression or tension forces.

The reinforcing bars 100, 101 also include load transfer connectors 105 (also referred to as "shear blocks"). In the optional embodiments illustrated in FIGS. 1-5, the load transfer connectors are rectangular. However, it is contemplated that the load transfer connectors 105 may take any shape such as round, oval, square, triangular, or the like. Likewise, while the optional embodiments illustrated in FIGS. 1-8 show two load transfer connectors 105 per reinforcing bar 100, 101, any quantity of one or more load transfer connectors 105 may be included. Likewise, the placement along the reinforcing bar 100, 101 could take any pattern or form. For example, in the optional embodiments illustrated in FIGS. 1-8, the load transfer connectors 105 are aligned along the long axis of the reinforcing bars 100, 101. However, this should be interpreted as merely illustrative, since it is contemplated that the load transfer connectors 105 could be placed in any location and with any pattern.

The load transfer connectors 105 illustrated in FIGS. 1-8 are attached to the reinforcing bars 100, 101. In the optional embodiments of FIGS. 1-5, the load transfer connectors 105 are attached to the surface of the reinforcing bars 100, 101. In the optional embodiment of FIGS. 6-8, the load transfer connectors 105 fit into openings 106 in a reinforcing bar 100. As discussed in greater detail below, the load transfer connectors 105 transfer loads between adjoining reinforcing bars 100, 101 of the reinforcing system. Thus, in the optional embodiments of FIGS. 1-8, the load transfer connectors 105 are located proximate to one end (FIGS. 4-8) or both ends (FIGS. 1-3) of each reinforcing bar 100, 101. However, it is contemplated that the load transfer connectors 105 could, in alternate optional embodiments, be additionally, or alternatively disposed along the surface of the reinforcing bars 100, 101 away from the ends of the reinforcing bars 100, 101. Again, it is contemplated that any quantity of load transfer connectors 105, of any shape and distributed in any manner, may be provided on the reinforcing bars 100, 101. In the optional embodiment of FIGS. 1-5, it is contemplated that the load transfer connectors 105 may be attached to the surface of the reinforcing bars 100, 101, such as by welding, or may be integrally formed with the reinforcing bars 100, 101. In the optional embodiment of FIGS. 6-8, it is contemplated that the load transfer connectors 105 may be fitted into openings 106 in each reinforcing bar 100, 101 to be connected.

A link plate 102 overlies the connection between reinforcing bars 100, 101. The link plate 102 includes openings 106 that mate with the load transfer connectors 105. In one optional embodiment, the openings 106 mate with the load transfer connectors 105 with an interference fit (also known as a friction fit or press fit, as those terms are understood in mechanical engineering). Alternatively, the mating connection between the openings 106 and load transfer connectors 105 may be a looser fit, e.g., a transition fit or running fit. The link plate 102 serves to transfer loads between adjoining reinforcing bars 100, 101 through the interface of the openings 106 and the load transfer connectors 105. Under load, the openings 106 of the link plate 102 bear against the load transfer connectors 105 of one or both of the underlying reinforcing bars 100, 101, or vice versa, thereby reinforcing the monopole 200. Specifically, as the monopole 200 is subjected to bending forces or moments, longitudinal tension or compression forces are created in the reinforcing bars 100, 101. These forces are transferred between the reinforcing bars 100, 101 through the load transfer connectors 105 and openings 106 of the link plate 102 that connect to the load transfer connectors 105.

Figure 2:
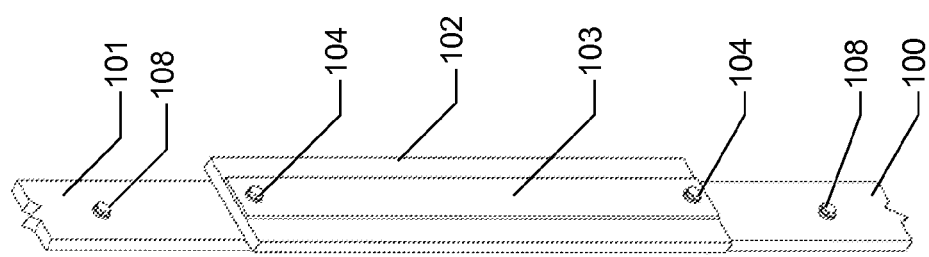
FIG. 2 is an elevated perspective view of an assembled link-plate according to an embodiment of the present invention.
Figure 1:
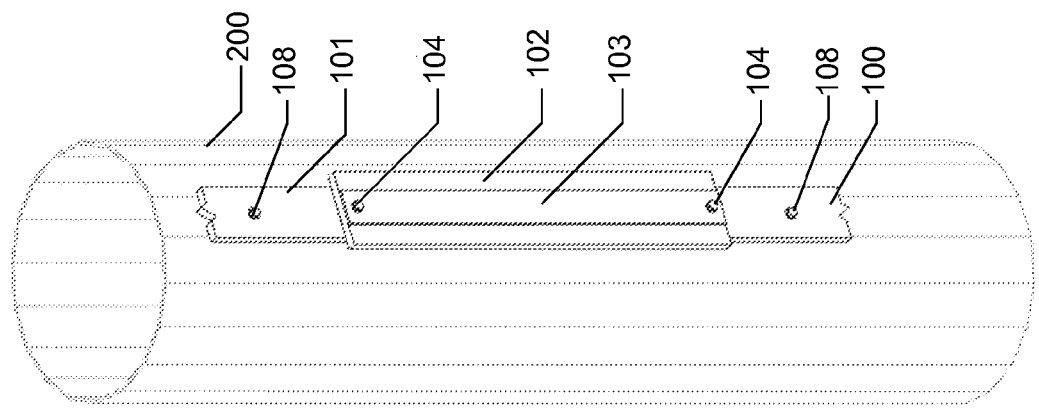
FIG. 1 is an elevated perspective view of a pole and assembled link-plate according to an embodiment of the present invention.
Figure 8:
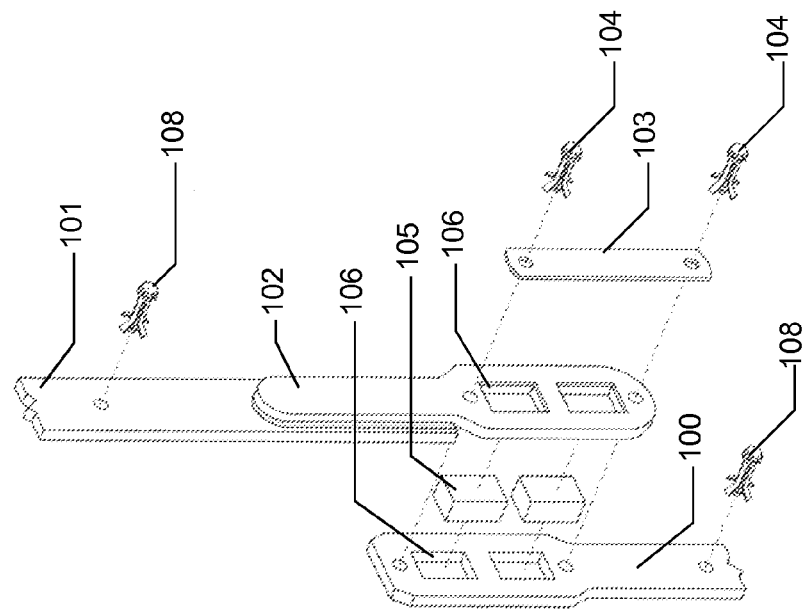
FIG. 8 is an elevated perspective assembly view of a link-plate according to an embodiment of the present invention.
Figure 7:
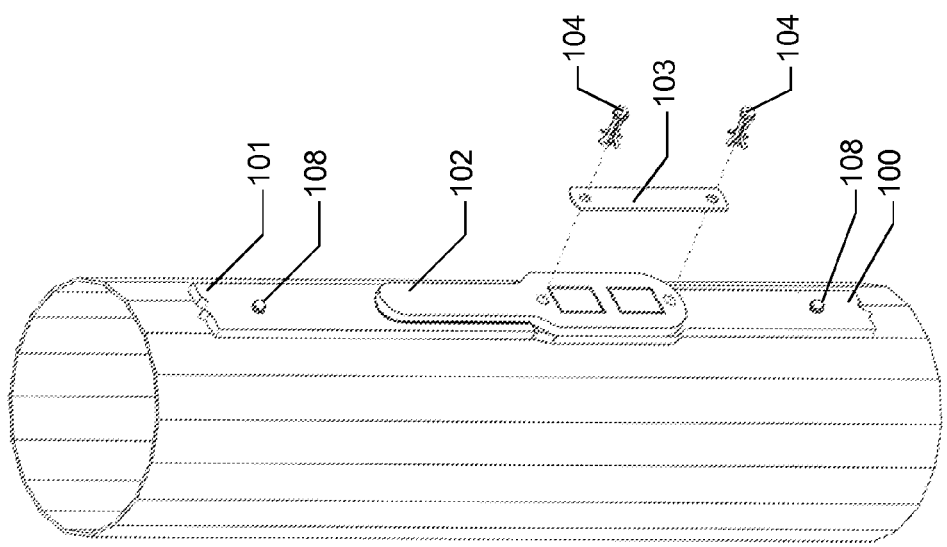
FIG. 7 is an elevated perspective view of a pole and assembled link-plate according to an embodiment of the present invention.
Figure 6:
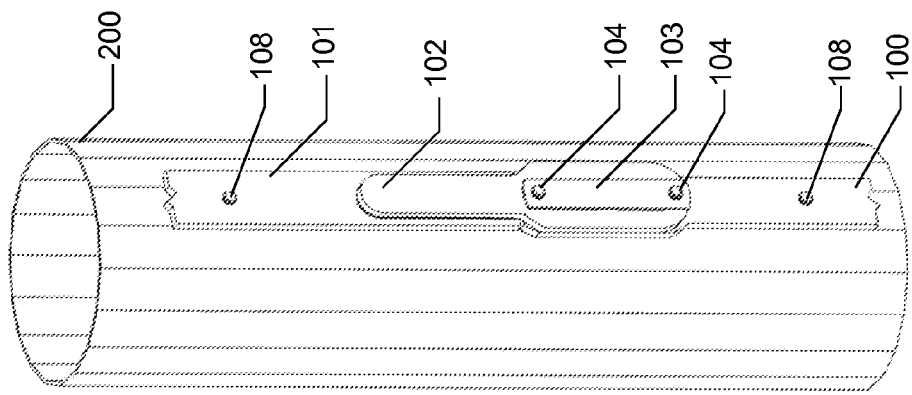
FIG. 6 is an elevated perspective view of a pole and assembled link-plate according to an embodiment of the present invention.

In the optional embodiment of FIGS. 1-3, the link plate 102 may include openings 106 that mate with load transfer connectors 105 on both reinforcing bars to be connected 100, 101. In another optional embodiment illustrated in FIGS. 4-8, the link plate 102 may be welded to (or otherwise attached to fastened to, or formed with) one reinforcing bar 100 with openings 106 to mate with load transfer connectors 105 on the other reinforcing bar 101 to be connected. As may be appreciated, the link plate 102 of such an optional embodiment may be attached (e.g., welded, fastened, or the like) to the reinforcing bar 100 in the shop prior to installation, in the field during installation, or any other time.

In an optional embodiment illustrated in FIGS. 1-5, a cover plate 103 overlies the link plate 102 that connects adjoining reinforcing bars 100, 101 to one another. In one such optional embodiment, the cover plate 103 may be held to the link plate 102 with fasteners 104, such as a Type HB Hollo-Bolt™ or other types of fasteners and such bolts were not intended to resist any of the longitudinal tension or compression forces but merely to secure the assembly together.

In use, reinforcing bars 100, 101 may be secured to a monopole 200 using bolts or other fasteners 108 that pass through the reinforcing bar 100, 101 and into the monopole 200. Adjoining reinforcing bars 100, 101 may be secured to one another by positioning a link plate 102 over the adjoining reinforcing bars 100, 101, with the openings 106 in the link plate 102 aligned with the load transfer connectors 405 of the underlying reinforcing bars 100, 101. The link plate 102 is secured to the reinforcing bars 100, 101 with the openings 106 mated to the load transfer connectors 105. As illustrated in FIGS. 1-3, the link plate 102 may mate with load transfer connectors 105 on both adjoining reinforcing bars 100, 101 through the openings 106 in the link plate 102. Alternatively, as illustrated in FIGS. 4 and 5, the link plate 102 may be secured to one of the reinforcing bars 100, such as through shop-welding or field-welding the link plate 102 to the reinforcing bar 100, and mated to the load transfer connectors 105 on an adjacent reinforcing bar 101 through the openings 106 in the link plate 102.

Referring generally to FIGS. 1-5, in an optional embodiment, a bolt 104 secures the link plate 102 to one or both of the underlying reinforcing bars 100, 101. In a further optional embodiment, a cover plate 103 may be secured over the link plate 102. to cover the mated openings 106 and load transfer connectors 105. In one such optional embodiment, a fastener 104 secures the cover plate 103, link plate 102, and reinforcing bars 100, 101 together.

Use of the link plate 102 would permit more standardization of parts as only a few link plate designs would be needed to properly splice many sizes and shapes of reinforcing bars 100, 101. Additionally, the link plate 102 could be used on many types of monopole structures, such as wind turbines, pipe poles, stepped poles, tapered poles, or the like. Additionally, using the link plate 102 would be more aesthetic as it would minimize the number of bolts used at the splices. The completed installation would appear more like one continuous reinforcing bar connected to the monopole structure. Thus, the present invention seeks to reduce the amount of drilling needed for splicing the reinforcing plates to thereby speed the installation of monopole reinforcing plates and reduce the cost of augmenting and reinforcing monopoles.

While certain embodiments of the present invention have been shown and described it is to be understood that the present invention is subject to many modifications and changes without departing from the spirit and scope of the claims presented herein.

I claim:

1. A device for reinforcing a monopole comprising:
   a plurality of reinforcing bars disposed to at least partially abut the monopole, each of the reinforcing bars having a surface opposite the monopole, wherein at least one of the reinforcing bars includes at least one load transfer connector disposed on the surface opposite the monopole and projecting away from the monopole; and
   a link plate having at least one opening shaped to mate with the at least one load transfer connector, such that adjacent reinforcing bars may be coupled by overlaying the link plate over the at least one of the reinforcing bars such that the link plate openings mate with the at least one load transfer connector, wherein at least a portion of the at least one of the reinforcing bars is interposed between the link plate and the monopole.

2. The device of claim 1 further comprising a cover plate positioned to overlie the at least one opening of the link plate while the link plate is mated with the at least one load transfer connector.

3. The device of claim 1 wherein the mating between the at least one opening of the link plate and the at least one load transfer connector is an unthreaded interference fit.

4. The device of claim 1 wherein the at least one load transfer connector is attached to the at least one of the reinforcing bars.

5. The device of claim 4 wherein the at least one load transfer connector is welded to the at least one of the reinforcing bars.

6. The device of claim 1 wherein the at least one load transfer connector is integrally formed with the at least one of the reinforcing bars.

7. The device of claim 1 wherein the at least one of the reinforcing bars includes the at least one load transfer connector disposed adjacent at least one end of the at least one of the reinforcing bars.

8. The device of claim 1 wherein the at least one of the reinforcing bars includes the at least one load transfer connector disposed proximate to a first end of the at least one of the reinforcing bars and wherein a second link plate is coupled to a second end of the at least one of the reinforcing bars opposite the first end.

9. The device of claim 1 wherein the at least one load transfer connector is attached to the surface of a first one of the reinforcing bars and the link plate is attached to a second one of the reinforcing bars.

10. The device of claim 1 wherein a second link plate is attached to the surface of the at least one of the reinforcing bars.

11. A device for reinforcing a monopole comprising:
    a plurality of reinforcing bars disposed to at least partially abut the monopole, each of the reinforcing bars having two ends and a surface, wherein each of the reinforcing bars includes at least one load transfer connector attached thereto proximate to at least one of the ends on a reinforcing bar surface opposite the monopole and projecting away from the monopole; and
    a link plate having openings shaped to mate with the load transfer connectors, such that adjoining reinforcing bars may be spliced by overlaying the link plate over at least one of the adjoining reinforcing bars and mating the link plate openings with the load transfer connectors of the at least one of the adjoining reinforcing bars, wherein at least a portion of the adjoining reinforcing bars is interposed between the link plate and the monopole.

12. The device of claim 11 further comprising a cover plate positioned to overlie the link plate openings while mated with the load transfer connectors.

13. The device of claim 11 wherein the mating between the link plate openings and the load transfer connectors is an unthreaded interference fit.

14. The device of claim 11 wherein at least one of the load transfer connectors is welded to at least one of the reinforcing bars.

15. The device of claim 11 wherein at least one of the load transfer connectors is integrally formed with at least one of the reinforcing bars.

16. The device of claim 11 wherein at least one of the load transfer connectors is attached to the surface of at least one of the reinforcing bars opposite a second surface that is configured to be disposed adjacent the monopole.

17. The device of claim 11 wherein the load transfer connectors are attached to the surface of the respective reinforcing bar opposite a second surface that is configured to abut the monopole.

18. A device for reinforcing a monopole comprising:
    a plurality of reinforcing bars disposed to at least partially abut the monopole, each of the reinforcing bars having two ends;
    a plurality of load transfer connectors, each disposed proximate to at least one of the ends of a respective one of the reinforcing bars on a reinforcing bar surface opposite the monopole and projecting away from the monopole; and
    a plurality of link plates having openings shaped to mate with the load transfer connectors, such that adjoining reinforcing bars may be spliced by overlaying one of the link plates over one of the ends of a first adjoining reinforcing bar to cause the openings of the one of the link plates to mate with the load transfer connectors disposed proximate to the at least one of the ends of a second adjoining reinforcing bar, wherein at least a portion of the adjoining reinforcing bars is interposed between the link plate and the monopole.

19. The device of claim 18 further comprising a cover plate positioned to overlie the openings of at least one of the link plates while mated with the load transfer connectors.

20. The device of claim 18 wherein the mating between the link plate openings and the load transfer connectors is an unthreaded interference fit.

21. The device of claim 18 wherein at least one of the load transfer connectors is attached to at least one of the reinforcing bars.

22. The device of claim 18 wherein at least one of the load transfer connectors is welded to at least one of the reinforcing bars.

* * * * *